United States Patent [19]

Weinberg

[11] Patent Number: 4,719,912

[45] Date of Patent: Jan. 19, 1988

[54] APPARATUS FOR CONTROLLING THE PHOTOCOAGULATION OF BIOLOGICAL TISSUE

[75] Inventor: Wolfram S. Weinberg, Rockingham, Tex.

[73] Assignee: Promed Technology, Inc., Dallas, Tex.

[21] Appl. No.: 57,692

[22] Filed: May 26, 1987

Related U.S. Application Data

[63] Continuation of Ser. No. 649,541, Sep. 11, 1984, abandoned.

[30] Foreign Application Priority Data

Feb. 28, 1983 [DE] Fed. Rep. of Germany .... P3306981
Feb. 27, 1984 [WO] PCT Intl.
  Appl. .................. PCT/US84/00295

[51] Int. Cl.$^4$ ............................................ A61B 17/36
[52] U.S. Cl. .................. 128/303.1; 128/395; 219/121 LA
[58] Field of Search ................. 128/6, 303.1, 395–398; 219/121 LH, 121 LB; 250/211 R, 332

[56] References Cited

U.S. PATENT DOCUMENTS

| | | | |
|---|---|---|---|
| 3,181,351 | 5/1965 | Stauffer | 351/200 |
| 3,689,159 | 9/1972 | Taniguchi et al. | 356/123 |
| 3,720,213 | 3/1973 | Hobart et al. | 128/395 |
| 3,795,784 | 3/1974 | Moll et al. | 219/121 LB |
| 4,091,814 | 5/1978 | Togo | 128/303.1 |
| 4,122,853 | 10/1978 | Smith | 128/303.1 |
| 4,149,787 | 4/1979 | Kobayashi et al. | 351/210 |
| 4,154,530 | 5/1979 | Connolly et al. | 219/121 L X |
| 4,164,686 | 8/1979 | Vital et al. | 315/241 |
| 4,215,694 | 8/1980 | Isakov et al. | 128/303.1 |
| 4,249,825 | 2/1981 | Shapiro | 356/223 |
| 4,289,378 | 9/1981 | Remy et al. | 128/395 |
| 4,350,163 | 9/1982 | Ford et al. | 128/633 |
| 4,438,765 | 3/1984 | Wilinsky | 128/395 |
| 4,564,012 | 1/1986 | Shimadi et al. | 128/395 |

FOREIGN PATENT DOCUMENTS

| | | | |
|---|---|---|---|
| 2620846 | 11/1977 | Fed. Rep. of Germany | 128/303.1 |
| 2829516 | 1/1980 | Fed. Rep. of Germany | 128/303.1 |
| 251860 | 2/1970 | U.S.S.R. | 35/1 |
| 555576 | 10/1977 | U.S.S.R. | 128/395 |

Primary Examiner—Kyle L. Howell
Assistant Examiner—Max F. Hindenburg
Attorney, Agent, or Firm—Crutsinger & Booth

[57] ABSTRACT

Apparatus to control the extent of photocoagulation of the retina wherein light reflected from discrete portions ($T_i$) of the retina (75) in the eye is projected by a lens system (82) to individual photodiodes (D1) in an array (85) to generate electrical signals related to the light intensity reflected from a corresponding portion ($T_i$) on the retina (75) being treated. A change in the reflectance of any discrete portion ($T_i$) of an area on the retina relative to the reflectance of any discrete portion of the area on the retina actuates a control mechanism associated with laser (22). Upon a change to a threshold reflectance or a maximum rate of change in reflectance, a control apparatus (90) automatically adjusts parameters of treatment including power (22), focus (25) or sighting (102, 104).

20 Claims, 5 Drawing Figures

APPARATUS FOR CONTROLLING THE PHOTOCOAGULATION OF BIOLOGICAL TISSUE

This is a continuation of application Ser. No. 649,541 filed Sept. 11, 1984, now abandoned.

The present invention relates to a process for controlling the coagulation of biological tissue and improvements in apparatus for controlling the coagulation of tissue of the type disclosed in German Application No. P30 24 169.1-35; in Documenta Ophthalmologica Proceedings Series 36- "Laser Treatment and Photocoagulation of the Eye," Proceeding of the International Symposium Munich, F.R.G. September 1982; and GSF-Bericht BPT 5, published by Gesellschaft Fur Strahlen- und Umweltforschung, Munich, West Germany, "Time Dependence of the Retina-Reaction during and after Laser coagulation with Various Coagulation Parameters." The method and apparatus are, for example, used in ophthalmology for the treatment of retinal diseases. However, the method may be used in processes wherein a change in reflectance of a surface results from treatment of the surface and the underlying material on which the surface is formed.

In the known process and the associated apparatus, the area or part of said area which is to undergo photocoagulation is imaged in the form of an intermediate image by means of an optical device. The light flux passing through a diaphragm installed in the intermediate image is proportional to the luminance prevailing in the diaphragm field and is supplied to a detector. This makes it possible to measure the average luminance prevailing in the complete area illuminated by the measuring radiation and imaged in the intermediate image, as well as its time change during the coagulation process. Typically, the time behaviour of the luminance has a certain "latent period", during which the luminance is initially constant, this being followed by a second phase in which the luminance increases linearly with time. Information is obtained from the length of the latent period and the size of the growth rate in the linear luminance increase phase, which enables forecasts to be made regarding the further course of the coagulation action. This makes it possible to influence the total coagulation action obtained during the actual irradiation, in that the exposure parameters are adapted in a planned manner during irradiation.

However, the known process can only be performed with satisfactory results, if either the absorption characteristics of the irradiated objects are known and/or are the same for all the irradiated areas, or if the intensity distribution of the coagulation irradiation at the location of the action is known and/or is constant for all the irradiations. Recent research has shown that conclusions can only be drawn on the energy quantities deposited in the absorption coatings when at least one of these prerequisites regarding the measurement of the latent period and the constant luminance growth rate at the start of the luminance change is known. Only then is it possible to forecast the further course of the irradiation action, which can be controlled by varying the irradiation parameters. The known process also assumes that the irradiation action and the extension of the coagulation zone can be adequately monitored, in that the luminance prevailing in the complete area imaged in the diaphragm in the intermediate image plane is measured. However, such an integral measurement, which supplies a mean value, cannot distinguish whether a narrowly defined partial area within the measured area has become brighter, i.e. the luminance has locally increased, or whether, in said area, the partial area in which an increased luminance exists has spread. This means that with the known process, a local coagulation, acting in the depth of the tissue, cannot be distinguished from a radial expansion or a radial extension of the coagulation zone of the surface of the tissue and both are in fact evaluated as the same reaction.

Under the normal conditions prevailing in the photocoagulation of biological tissue, for example in the case of retina treatment with intense light, neither are the absorption characteristics, which can vary widely, known or obtainable by measurement, or is it possible to reliably adjust and control the intensity distribution of the coagulation radiation at the point of action, because it is often considerably impaired by fine irregularities in transmitting and imaging media. In addition, both the intensity distribution and the absorption and consequently the effectiveness of the irradiation, can be greatly impaired by inhomogeneities, such as differences in the tissue structure or the nature of the tissue, or also portions of adjacent, already coagulated areas within the area irradiated with the intense light source. The imaging and transmission conditions for the intense light irradiation also locally vary in different ways with the increase in the light scattering in the coagulated area during the coagulation process. These local differences cannot be individually determined with the integral measurement of the luminance, which merely supplies a mean value for the total surface area illuminated by the measuring beam. Moreover, incorrect measurement of the luminance caused by reflections of the measuring beam on other surfaces of the measuring system, i.e. the illuminating and measuring optics are only detected if made apparent by considerable divergences from the customary values.

Thus, the problem of the invention is to provide a process making it possible to determine local differences within the area to be measured and more particularly making it possible during the coagulation process to distinguish whether the luminance has locally increased in a partial area or whether said partial area has increased in size with increased luminance.

The invention is based on the finding that the increase in the luminance during the coagulation of biological tissue is a measure of the size of the volume of the coagulated tissue, in accordance with the relation:

$$R = p V$$

in which R is the luminance increase in the coagulated area and V the volume of the coagulated tissue, while p is a coefficient, which is dependent on the nature of the tissue and can be experimentally determined. The measurement of the local distribution of the luminance in the coagulation area makes it possible to precisely establish which volume has been assumed by the coagulated area. This evaluation can take place during irradiation and it is then possible to reliably control the intense light source and its imaging optics and consequently the coagulation action.

The process according to the invention makes it possible to determine irregularities in the intense light irradiation and/or measuring radiation, which are for example due to reflections and/or limitations to the radiation in the optical system. These irregularities can be detected by means of the pattern of the local luminance distribution. In particular, the process according to the invention advantageously makes it possible to determine the depth of the coagulation action in a given partial area if its surface is known and the ratio of the luminance to the size of the tissue volume re-emitting the light is known on the basis of experimental investigation.

The process according to the invention also has the advantage that it can detect irregularities in the spatial extension of the coagulation zone, which can be taken into consideration during the control.

The performance of the process according to the invention leads to the following advantages:

1. With the formation of the quotients of the luminances in the partial areas, it is possible to determine the relative luminance distribution and consequently also the relative size of the local irregularities, which in turn make it possible to discriminate inhomogeneities of the object and interferences in the irradiating and measuring optics.

2. On the basis of this information and using the regulating member 19 and the sighting unit, it is possible to correct the distribution in which the intense light source and/or measuring radiation source is imaged on the measured area, while also making it possible to select the target area.

3. By subtracting the relative luminance changes in the partial areas and/or partial area groups, it is possible to determine relative divergences with respect to the symmetrical coagulation action.

4. By subtracting the relative luminances, time interval of the latent periods and the time gradients of the luminance changes in the partial areas and/or partial area groups, it is possible to determine the spatial gradients of the coagulation action.

5. By forming the quotients of the luminances, time interval of the latent periods and tne time gradients of the luminance changes in the partial areas and/or partial area groups, it is possible to determine relative divergences with respect to the symmetrical spread of the coagulation action.

6. By comparing the measured local luminances, and the magnitudes determined therefrom with predetermined values, it is possible to fix limits for the coagulation action which, if exceeded, can have undesired effects.

7. By combining the partial areas into partial area groups, it is possible to reduce the quantity of data to be processed and consequently the measurement and control of the expected coagulation action can be adapted as regards time and space.

8. Time adaptation of the measurement and control of the expected coagulation action is made possible by the variable selectable scanning rates of the luminances.

9. The use of solid-state image sensors involves employing known technology, which is particularly suitable for performing the process according to the invention when combined with laser treatment apparatus and a precise computerized control circuit.

10. By measuring the luminance in the transmission, it is possible to measure and control the coagulation action with increased sensitivity with respect to its extension in the depth of the tissue.

DESCRIPTION OF DRAWING

The invention is described in greater detail hereinafter relative to a preferred embodiment of the invention illustrated in the attached drawings, wherein.

Numeral references are employed to designate like parts throughout the various figures of the drawing.

DESCRIPTION OF A PREFERRED EMBODIMENT

Figure 1:
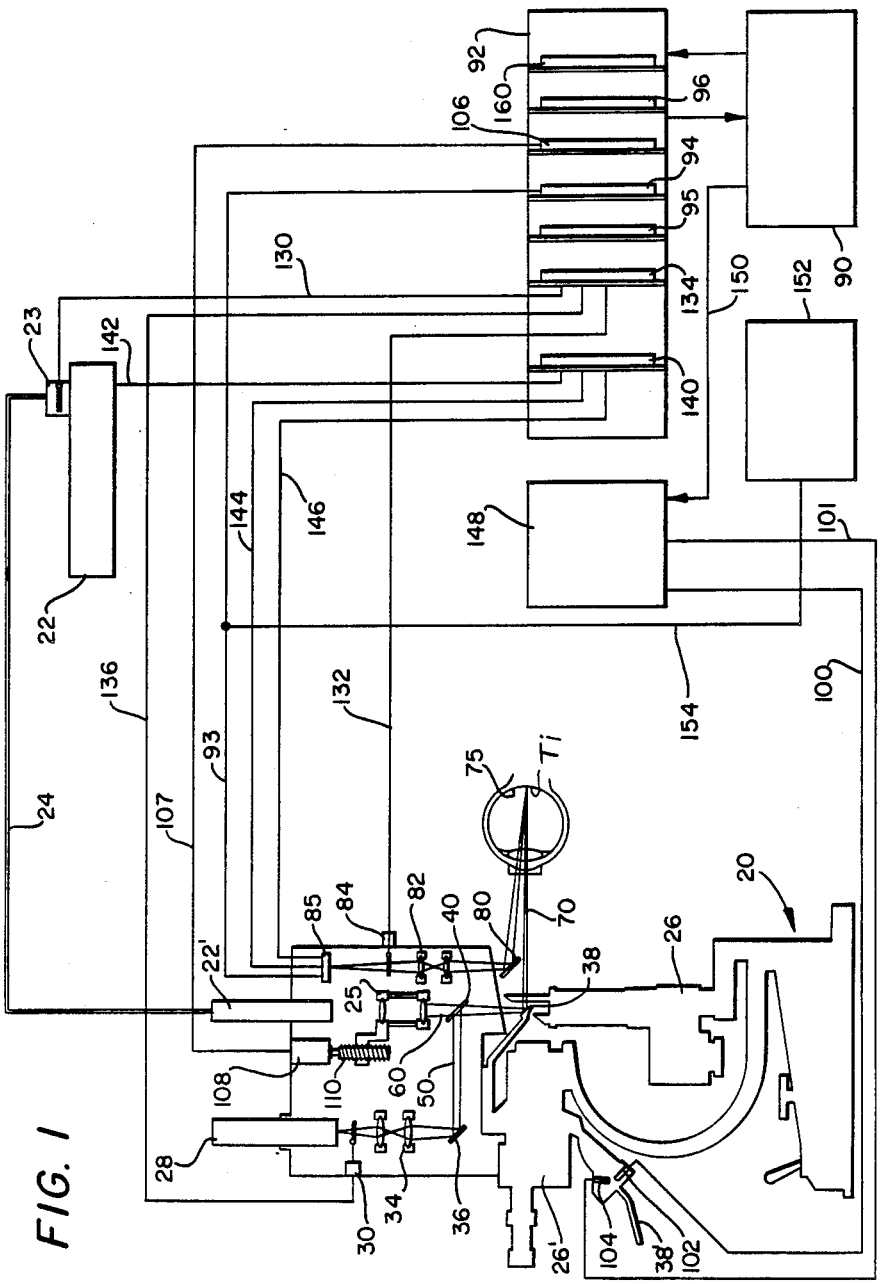
FIG. 1 is a diagrammatic view of the apparatus.

Referring to FIG. 1 of the drawing, the numeral 20 generally designates apparatus which may be employed for accomplishing the process described herein. The apparatus includes an argon laser 22 connected through a flexible fiberoptic cable 24 and a connector tube 22' connectable to a slit lamp 26 and microscope 26' of a type which are commercially available from Coherent Medical Group of Palo Alto, Calif., and is referred to as Innova 910 ophthalmic photocoagulator and multipurpose laser system.

The argon laser 22 produces the treatment beam of light of approximately 4.0 watts of blue-green argon light having a wave length of 488 and 514 nanometers (nm) or 1.5 watts of green-only argon light with green-only option having a wave length of 514 nm. The lens structure is adjustable to provide spot sizes ranging from 50 to 2,000 microns. A control module permits adjustment of power levels and adjustment of the spot size. Since argon lasers and slit lamps for use as a photocoagulator are well known to persons skilled in the art, further description of this aspect of the apparatus is not deemed necessary. An early form of a similar laser photocoagulator is disclosed in U.S. Pat. No. 3,720,213.

The slit lamp 26 is preferably of the type commercially available from Carl Zeiss, Inc. of New York City, N.Y., and distributed as a "Slit Lamp 30 SL-M" which is conventionally used by ophthalmologists for examination and treatment of eyes.

The exposure time of the argon laser 22 is controlled by a shutter controller 23, as will be hereinafter more fully explained, which is provided as a component of the argon laser 22 but controlled by a computer circuit.

A helium-neon laser 28 preferably has a power output of 0.5 mW and forms a beam having a wave length of 632 nm to function as a pilot laser. A suitable laser is commercially available from Newport Corporation of Fountain Valley, Calif. and is distributed under the trademark Spectra-Physics HeNe Laser Model Sp-155A. An electronic shutter 30 is mounted to selectively interrupt the light beam measuring radiation emitted from the pilot laser 28. A suitable shutter is available from Newport Corporation and is generally referred to as a Model 884 Electronic Shutter featuring a 6 mm diameter open aperture, black teflon-coated plates rated at up to one watt and one millisecond minimum open time.

A mounting system including a lens holder (not shown) is employed for supporting a lens system 34 and mirror 36 and a beam splitter 40 as illustrated in FIG. 1 of the drawing for combining the beam 50 of the helium-neon laser with the beam 60 of the argon laser to form a combined beam 70 which is directed into the eye by a mirror 38 on the slit lamp 26. The combined beam 70 impinges against tissue such as the retina in the posterior aspect of the eye or other tissue. The mirror 38 is manually controlled by a joy stick 38' or remotely controlled by horizontal and vertical actuators 102 and 104 as will be hereinafter more fully explained.

Light from the combined beam 70 from lasers 22 and 28 is reflected from surface 75 in the eye and delivered by a mirror 80 through a lens system 82 and a filter 84 to a two dimensional photodiode array 85. Each photodiode in array 85 generates electrical signals related to the light intensity reflected from a corresponding portion of the area on surface 75. A suitable photodiode array is available from Reticon Corporation of Sunnyvale, Calif., which is a subsidiary of EG&G, Inc. of Wellesley, Mass. The photodiode array is distributed as EG&G Reticon RA100×100A and is a two-dimensional self-scanned optical sensor array which has 10,000 diodes arranged in a 100×100 matrix. Diode spacing is on sixty micron centers in either dimension. Scanning is by means of two shift registers, one running at a sample rate and the other at a line rate. The maximum sample rate is 10 MHz. The individual diodes are packaged in a twenty-four pin dual-in-line package with a ground and polished window covering the mask-defined active area.

A MOS dynamic shift register sequentially selects the diode rows while two bucket brigades select the diodes from each column. Each position of the shift register selects two diode rows through two multiplexing gates, one for the odd and the other for selecting the even. This property of odd and even selection gives the array an added feature by providing the user the choice of selecting the odd and even fields.

Together the shift register and the bucket brigade process the signal. The shift register selects rows by a clock. The transfer gates parallel transfer the selected diode in each column into the bucket brigade. One bucket brigade obtains information from odd and the other bucket brigade the information from even diode columns. Each bucket brigade then shifts that information sequentially to the output.

The system hereinbefore described is controlled by a computer 90 which processes data received from the photodiode array 85 and controls the lasers 23 and 28.

A suitable treatment control apparatus is embodied in computer 90 for controlling the apparatus is a Hewlett Packard, Model 26S computer, product number HP9826S equipped with a multi-programmer main frame 92 (Hewlett Packard Model 6944A) and plug-in cards to provide the required control functions.

Analog-to-digital converter card 94 (Hewlett Packard 69759A) measures bipolar DC voltages and return the digitized value to the controller to indicate the magnitude and sign of the measured voltage on cable 93 connected to the photodetector array 85. Up to 100,000 readings per second can be transferred from the A/D converter 94 to a Hewlett Packard 69791A memory card 95 (via the external data outputs). Each reading can be initiated by program commands or by an external trigger signal.

A timer/pacer card 96 (Hewlett Packard Product No. 69736A) provides an output which is a programmable pulse from one microsecond to 18 hours in duration. In the normal mode, the output is a single pulse that can be used as a programmable delay. This card controls and triggers the other cards in the system.

A stepping motor controller card 106 (Hewlett Packard Product No. 69735A) delivers current through cable 107 to energize stepping motor 108 to rotate a screw 110 for adjusting the spacing between the lenses of the laser focusing lens system 25 in the argon laser 22.

A relay output card 134 (Hewlett Packard Product No. 69730A) is connected through line 130 to shutter 23 of the argon laser 22 and through lines 132 and 136 to filter 84 and shutter 30. This circuit operates as a flip-flop such that when shutter 30 is open to pass the light beam from the HeNe laser 28, the filter 84 is in position to pass only light having a wave length of 632 nm. When shutter 30 is closed, the filter 84 is moved to an inactive position to pass reflected light from the argon beam.

A digital output card 140, having sixteen separate channels, is connected through cable 142 to control power of the laser 22 and through cables 144 and 146 to the photodiode array 85.

A remote control module and interface 148 (Newport Corporation 855C Programmable Controller) is connected to the computer 90 by a cable 150 and delivers pulses through cables 100 and 101, respectively, to actuators 102 and 104 for moving the joy stick controller 38'.

A video monitor 152 is connected through cable 154 to cable 93 to display the output of the photodiode array 85. This output provides for visual observation of the tissue in surface 75 in the eye.

An interrupt card 160 is controlled by a suitable software program to initiate the digital output functions which are controlled by output cards 140 and 134.

The manufacturer's descriptions and specifications of the various computer and laser devices referred to above are incorporated herein by reference for all purposes.

Figure 2:
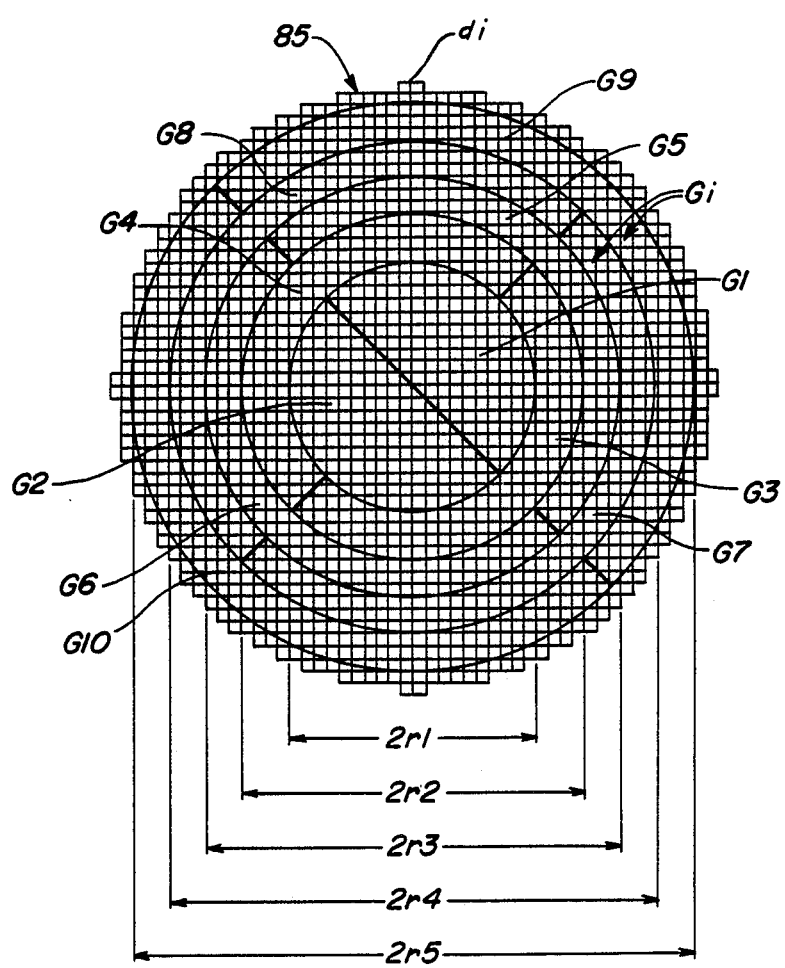
FIG. 2 is an enlarged elevational view of an array of photodiodes or an arrangement of individual light detectors.
Figure 3:
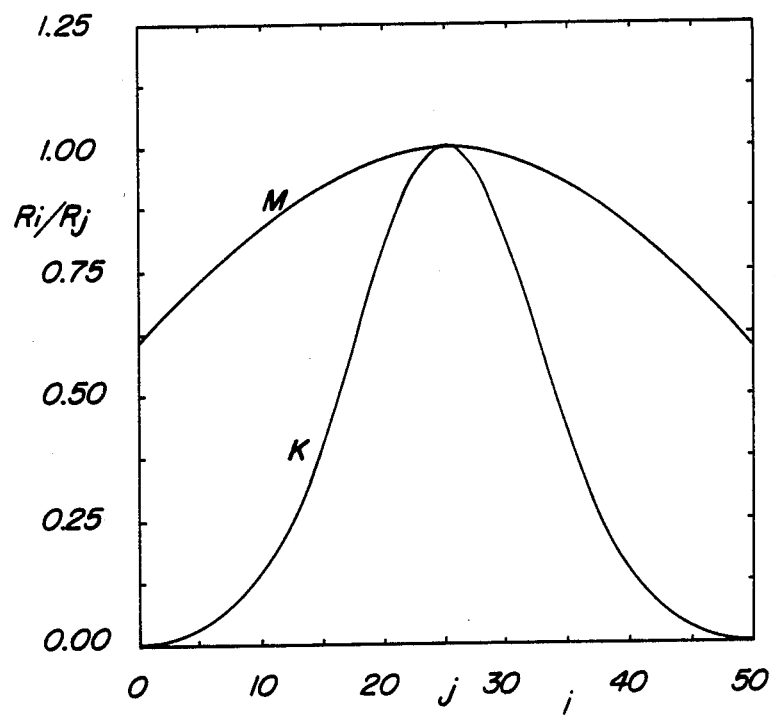
FIG. 3 is a graph diagrammatically indicating the spatial intensity distribution of the intense light of a first laser reflected from an area and a second laser reflected from the area measuring radiation, as can be determined by means of detectors arranged along a diameter of the detector surface to indicate the light intensity across the irradiated surface.
Figure 5:
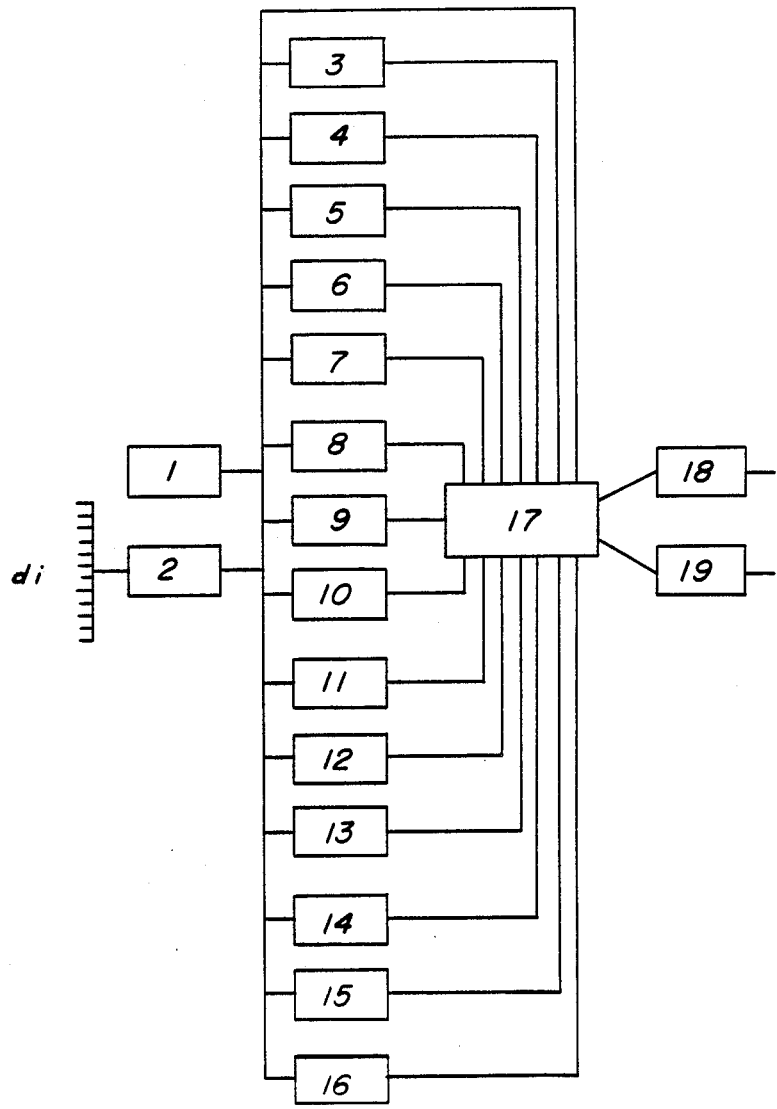
FIG. 5 a block circuit diagram of the evaluation and control circuit.

Firstly, the irradiation optics of the argon laser intense light source 22, as well as the photodiode detector device 85 and the helium-neon laser 28 for measuring the local luminance distribution is aligned by adjusting the patient and rotating the microscope with the area in which coagulation is to take place. Thus, this area is also imaged in the plane, in which is located the detector elements di in the photodiode array 85 corresponding to the center of the irradiated surface area as illustrated in FIG. 2. The local luminance distribution, which still does not have an effective intensity within this area due to the irradiation with the intense light source is measured by interrogating each of the photodiode detectors di in the array 85 which, by means of the selection circuit element according to the block diagram of FIG. 5, are connected via a data bus with the various evaluation circuits. By the formation of the quotients Ri/Rj of the luminances Ri in the individual partial areas Ti represented by each photodiode light detector element by the largest luminance Rj in the partial area Tj, the relative luminance distribution and consequently the relative local intensity distribution of the coagulation radiation are determined. Then, the relative local luminance distribution of the measuring radiation is determined in the same way. FIG. 3 shows a cross-section of the luminance distributions of the sub-threshold intense light radiation K of the argon laser 22 and the measuring radiation M of the helium-neon laser 28.

On the basis of each of these measured local distributions, a check is made by comparing the known distributions whether and to what extent irregularities are present. Their divergence from the predetermined distribution patterns are recognized by forming differences $R_i$-$R_j$ of the luminances $R_i$, $R_j$ in the adjacent partial areas $T_i$, $T_j$ with equal distances from the partial area with the maximum luminance. On the basis of the size and location of the irregularity in the distribution pattern, conclusions can be drawn regarding their cause as an inhomogeneity in the tissue and/or interference in the irradiation and imaging optics.

On the basis of these luminance distributions of the measuring radiation, the field illuminated by said measuring radiation is combined into $m=10$ partial area groups $G_i$ of photodiodes $d_i$ of array 85 by corresponding linking of individual adjacent detector elements. These represent half-ring surfaces of equal area with the same number of diodes in each half-ring area, which are concentric to the partial area with the maximum luminance and with increasing distance from said center, and are in each case displaced by 90° (of FIG. 2). A check is made beforehand by comparing the luminance distributions of the intense light irradiation and the measuring radiation to establish whether the area illuminated by the latter also covers in the intended manner the area irradiated by the intense light source. The luminance R1 prevailing in the partial area groups $G_i$ is then retained as values $R_{oi}$ at the start of coagulation irradiation and before coagulation is started with a preselected and now effective irradiation intensity.

Figure 4:
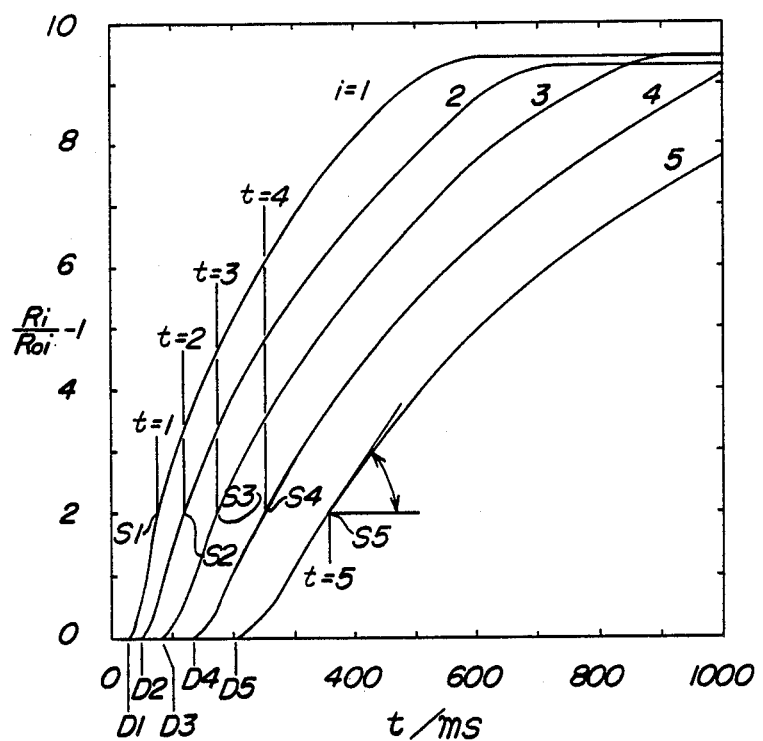
FIG. 4 a diagram in which the luminance increase within the individual partial area groups is plotted during an irradiation with a constant intensity distribution up to 1000 ms and relative to time.

During the following coagulation irradiation, the relative luminance $R_i/R_{oi}$ is measured at regular intervals in the individual partial area groups $G_i$. The number of measuring times, at the end of which the relative luminance $R_i/R_{oi}$ in the partial area group $G_i$ is greater than 0.1 for the first time, is the latent period $D_i$ (of FIG. 4). After the latent period $D_j$ in another area group $G_j$ has been determined, by subtracting the latent periods $D_i$-$D_j$ of the luminance change in adjacent partial area groups $G_i$, $G_j$ within the different radii (of FIG. 2, e.g. $i=4$, $j=2$), it is possible to determine the speed of the radial extension of the coagulation zone. By forming the quotients $D_i/D_j$ of the latent periods of partial area groups $G_i$, $G_j$ within the same radii (of FIG. 2, e.g. $i=3$, $j=4$), it is possible to determine the relative difference in the radial propagation rate in different directions. The luminance in the individual partial area groups then increases firstly with a rising and then with a falling increment rate $S_i$ (FIG. 4). For example, S5 in FIG. 4 indicates the slope or rate of change of the relative intensity of light reflected to a specific group of photodiodes in the array 85. This is determined as the gradient of the luminance change. The number of measuring time intervals up to the time when the increment rate $S_i$ in the partial area group $G_i$ decreases again for the first time, represents time "tsi." The interval between this time and the end of the latent period is dependent both on the irradiation intensity prevailing in this partial area group, the energy which has taken place there and the size of said partial area group.

Conclusions can be drawn regarding the ratio of the local coagulation action to its radial extension on the basis of experimental investigations based on the differences of the gradients of the luminance change in the partial area groups at different distances from the irradiation center. The relative difference in the coagulation action in the case of the asymmetrical formation of the coagulation zone can be established by forming the quotients of the gradients of the luminance change in two partial areas and at the same distance from the irradiation center. By subtracting the gradients of adjacent partial area groups at different distances from the center, on the basis of the 90° displacement, it is possible to further define the direction of the irregular spread. On the basis of experimental investigations, it is possible to forecast the further course of the luminance change and consequently also the spatial spread of the coagulation zone from the size of the latent period $D_i$ and the gradients of the luminance change $S_i$ at time "tsi," as well as the time interval $tsi$-$D_i$ (FIG. 5). As soon as the saturation value of the luminance change is reached within any one of the partial area groups, this value marks the complete coagulation of the tissue volume, whose surface is represented within this partial area group.

On the basis of this information, which can be determined at a very early stage of the coagulation action on subdividing the detector area into correspondingly small concentric surfaces around the radiation center, the further course of the coagulation spread can be regulated by a planned change to the radiation intensity and/or the radiation time and/or the diameter of the area irradiated by the intense light source.

At the end of the coagulation and while constantly measuring the luminance distribution in a predetermined direction, the irradiation and measuring optics can be moved by using the actuators 102 and 104 so far out of the previous irradiation field that it is possible to measure a distribution pattern, which is not impaired any more than intended by projecting in of the previous coagulation zone. This permits rapid coagulation in reliable uniform intervals, as is frequently required in practice.

FIG. 5 diagrammatically shows a block logic circuit diagram of the evaluation and control circuit. It compresses a timer 1 and a selection circuit 2 for selecting and interrogating detectors $D_i$. The outputs of the timer and the selection circuit are connected across a data line with the individual circuits 3–16 and logic circuit 17, which determine the aforementioned quantities, e.g. the relative luminance, its time and spatial gradient, etc. The outputs of circuit 3–16 are connected to the inputs of a logic circuit. From the data fed in, the logic circuit determines control data for the regulating units 18, 19 connected thereto, which in turn act on the intense light source 22, as well as its imaging optics and the sighting unit.

The mathematical calculations described above and outlined in the logic diagram illustrated in FIG. 5 are accomplished by the software program in the computer 90. Having described the details of the cards in the computer circuit, further description of the manipulation of the data in the memory of the computer is not deemed necessary.

Having described my invention, I claim:

1. Apparatus for performing photocoagulation of biological tissue comprising: an intensive light source for initiating coagulation; first optical means for focusing the intensive light source on an area to be irradiated; second optical means for projecting an image of the irradiated area; luminance measuring means, said second optical means projecting the image of the irradiated area onto said luminance measuring means, said measuring means being adapted to detect the luminance of at least two sub-regions of a region of the tissue; processing means adapted to generate control signals indicative of the change in luminance in each sub-region; control means supplied with the control signal for controlling the parameters of irradiation; a sighting device for shifting the beam of the intensive light source across the tissue; said control means controlling the intensity of the beam of the intensive light source and the position of the beam established by the sighting device.

2. A device according to claim 1, said processing means deriving control signals from relative measured values resulting from the quotient of the measured values with their respective values at the beginning of the coagulation irradiation.

3. A device according to claim 2, said processing means deriving control signals from at least one delay time lapsing from the beginning of the coagulation irradiation to the point of time when a relative measured value becomes greater than unity.

4. A device according to claim 1, said control means comprising: a first control means controlling the focusing of the optical means.

5. A device according to claim 1, said processing meaning detects the luminance changes of the sub-regions in terms of time and generating control signals therefrom.

6. A device according to claim 5, said processing means detecting the gradient of the luminance change of sub-regions in terms of time and generating control signals therefrom.

7. A device according to claim 6, said processing means detecting the difference of two gradients and generating control signals therefrom.

8. A device according to claim 5, wherein said luminance measuring means comprises: a photodetector array consisting of a field of two-dimensionally disposed detector elements.

9. A device according to claim 8, said detector elements detecting the reflected light of the intensive light source for measuring the luminance.

10. A device according to claim 8, said photodetector detecting the light passing through the biological tissue and measuring the luminance thereof.

11. A device according to claim 8, said control means comprising: a first control means controlling the focusing of the optical means.

12. A device according to claim 8, wherein an image of the region is formed on a single photodetector element, and the measuring beam successively irradiates the individual sub-regions.

13. A device according to claim 5, said control means comprising: first control means controlling the focusing of the optical means.

14. A device according to claim 1, wherein said luminance measuring means comprises: a photodetector array consisting of a field of two-dimensionally disposed detector elements.

15. A device according to claim 14, wherein an image of the region is formed on a single photodetector element, and that the measuring beam successively irradiates the individual sub-regions.

16. A device according to claim 14, said photodetector detecting the light passing through the biological tissue and measuring the luminance thereof.

17. A device according to claim 14, said control means comprising: a first control means controlling the focusing of the optical means.

18. A device according to claim 14, said detector elements being adapted to detect the reflected light of the intensive light source for measuring the luminance.

19. Apparatus to control the extent of treatment of a target area by treatment apparatus comprising: treatment apparatus including a light source; means to direct light from the light source to the target area to be treated by the treatment apparatus; an array of photodiodes; means to direct light reflected from each of a plurality of discrete portions of the target area to corresponding photodiodes in the array; and control means associated with the array of photodiodes and the treatment apparatus to adjust treatment apparatus parameters of treatment of the target area when the reflectance of any of the discrete portions of the target area changes to a predetermined relationship relative to the reflectance of the same or any other discrete portion of the target area.

20. Apparatus to control the extent of intensive light treatment of a target area in tissue by treatment apparatus including a pilot light source; means focusing said pilot light source to illuminate an area around a target area; a treatment light source, said treatment light source delivering a beam having a wave length different from the wave length of said pilot light source; means focusing said treatment light source on the target area inside said illuminated area; an array of photodiodes; filter means to direct light from said pilot light reflected from each of a plurality of discrete portions of the illuminated area including the target area to corresponding photodiodes in the array; and control means associated with the array of photodiodes and the treatment apparatus to terminate treatment of the target area when the reflectance of any of the discrete portions of the target area resulting from changes in the tissue in the target area changes to a predetermined relationship relative to the reflectance of the same discrete portion of the target area or any other discrete portion of the target area.

* * * * *